United States Patent
Bennett et al.

(10) Patent No.: US 9,549,509 B2
(45) Date of Patent: Jan. 24, 2017

(54) GLK GENES FOR IMPROVED FRUIT QUALITY

(71) Applicant: THE REGENTS OF THE UNIVERSITY OF CALIFORNIA, Oakland, CA (US)

(72) Inventors: Alan B. Bennett, Davis, CA (US); Ann L. T. Powell, Davis, CA (US); Theresa A. Hill, Davis, CA (US); Kalai Lam Cheng, San Francisco de Dos Rios San Jose (CR); Rosa E. Figueroa-Balderas, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 222 days.

(21) Appl. No.: 14/350,753

(22) PCT Filed: Oct. 10, 2012

(86) PCT No.: PCT/US2012/059600
§ 371 (c)(1),
(2) Date: Apr. 9, 2014

(87) PCT Pub. No.: WO2013/055821
PCT Pub. Date: Apr. 18, 2013

(65) Prior Publication Data
US 2014/0380517 A1 Dec. 25, 2014

Related U.S. Application Data

(60) Provisional application No. 61/546,934, filed on Oct. 13, 2011.

(51) Int. Cl.
| | |
|---|---|
| *A01H 1/04* | (2006.01) |
| *A01H 5/00* | (2006.01) |
| *A01H 1/02* | (2006.01) |
| *A01H 5/08* | (2006.01) |
| *C07K 14/415* | (2006.01) |

(52) U.S. Cl.
CPC ............ *A01H 1/02* (2013.01); *A01H 1/04* (2013.01); *A01H 5/08* (2013.01); *C07K 14/415* (2013.01)

(58) Field of Classification Search
None
See application file for complete search history.

(56) References Cited

U.S. PATENT DOCUMENTS

| | | |
|---|---|---|
| 7,109,033 B2 | 9/2006 | Harper et al. |
| 2004/0034888 A1 | 2/2004 | Liu et al. |
| 2004/0216190 A1 | 10/2004 | Kovalic |
| 2009/0241218 A1 | 9/2009 | Frankard et al. |
| 2010/0154078 A1* | 6/2010 | Powell ............... C07K 14/415 800/282 |

OTHER PUBLICATIONS

Palca, 2010, Taking Tomatoes Back to Their Tasty Roots, NPR, 1-4.*
Frary et al, 2010, BMC, Plant Biology, 10:1-16.*
Bravo-Garcia et al, 2009, New Phtyologist, 183:133-141.*
International Search Report and Written Opinion dated Mar. 29, 2013 for International Patent Application No. PCT/US2012/059600, 19 pages.
Waters et al., "GLK transcription factors regulate chloroplast development in a cell-autonomous manner", The Plant Journal, vol. 56, pp. 432-444 (2008).

* cited by examiner

*Primary Examiner* — Jason Deveau Rosen
(74) *Attorney, Agent, or Firm* — Kilpatrick Townsend & Stockton LLP

(57) ABSTRACT

The present invention provides methods for improving fruit quality in plants that have low or reduced levels of Golden2-like (GLK) activity in the green fruit (e.g., cultivated tomato). The methods involve introgressing genes encoding functional GLKs into the plant so that they are expressed in the green fruit of the plant and thereby increase chloroplast biogenesis in the fruit. The plants of the invention have improved fruit quality, such as increased levels of starch, soluble solids, and/or sugars.

6 Claims, No Drawings

SEQUENCE LISTING

```
<160> NUMBER OF SEQ ID NOS: 8

<210> SEQ ID NO 1
<211> LENGTH: 934
<212> TYPE: DNA
<213> ORGANISM: Solanum lycopersicum
<220> FEATURE:
<223> OTHER INFORMATION: Solanum lycopersicum cultivar Craigella
      non-functional Golden2-like 2 (GLK2, SlGLK2) truncation mutation
      nuclear transcription factor, GARP family transcription factor

<400> SEQUENCE: 1
atgcttgctc tatcttcatc attgagctac aaaaatgaaa gggaaaatta tgatttattc       60
caagattttt cccatgggaa tttaatcgac accatcaatt tcgatgactt tttcgatgaa      120
atcaacggtg gagatttact gccagatttc gaaattttt gtgaagaacc tgctattcat      180
ggaaatatga aatctaagtc aaaagaagct aaaaaaatca tctagcaaaa tcaaaaatcc      240
tcaaggaaag aaaaaagtaa agttggattg gactccagag ctacatagga aatttgtaaa      300
agcaatagag aaattaggtg ttgataaggc agtcccatca agaattttgg agcttatggc      360
aactcatggt ctcactagac ataacattgc tagtcatctt caaaaatatc gagctcatcg      420
aaaacattta ctagcgagag aagctgaagc agcgagcttg aaccatagga agcaaatgta      480
tagcggagcc accacaatcg gaggcggagg aaagagaatt ttgatgaacc cctggcccgc      540
accgccaacc atgggtttcc cacccatggc tcatcatgtt agacccttac atgtttgggg      600
gcatccacat gtaaataatt cattttggca tccacattat caaagggtat cgaattctct      660
tgtaccaggc actccttgtt tttctgcgcc aataacatca gcgagatttg cagcacctct      720
catggtccca ggcatcccac caagccctgc catcatcaaa gttgacacag ttgcctctga      780
tttgcacccc tcaaatgaga gcatagatgc agctattgaa gatgttttat caaagccaca      840
attgccactt cccataggac tcaaacctcc atcaattgac agtgtgttga atgaattaca      900
acgtcaaggg attaccaaaa taccccaac ttga                                  934
```

```
<210> SEQ ID NO 2
<211> LENGTH: 933
<212> TYPE: DNA
<213> ORGANISM: Solanum pimpinellifolium
<220> FEATURE:
<223> OTHER INFORMATION: Solanum pimpinellifolium functional
      Golden2-like 2 (GLK2) nuclear transcription factor

<400> SEQUENCE: 2
atgcttgctc tatcttcatc attgagctac aaaaatgaaa gggaaaatta tgatttattc      60
caagattttt cccatgggaa tttaatcgac accatcaatt tcgatgactt tttcgatgaa     120
atcaacggtg gagatttact gccagatttc gaattttttt gtgaagaacc tgctattcat     180
ggaaatatga aatctaagtc aaaagaagct aaaaaatcat ctagcaaaat caaaaatcct     240
caaggaaaga agaaagtaaa gttggattgg actccagagc tacataggaa atttgtaaaa     300
gcaatagaga aattaggtgt tgataaggca gtcccatcaa gaattttgga gcttatggca     360
actcatggtc tcactagaca taacattgct agtcatcttc aaaaatatcg agctcatcga     420
aaacatttac tagcgagaga agctgaagca gcgagcttga accataggaa gcaaatgtat     480
agcggagcca ccacaatcgg aggcggagga agagaatttt tgatgaaccc ctggcccgta     540
ccgccaacca tgggtttccc acccatggct catcatgtta gacccttaca tgtttggggg     600
catccacatg taaataattc attttggcat ccacattatc aaagggtatc gaattctctt     660
gtaccaggca ctccttgttt tcctgcgcca ataacatcag cgagatttgc agcacctctc     720
atggtcccag gcatcccaca aagccctgcc atcatcaaag ttgacacaat gcctctgat      780 ttgcacccct caaatgagag catagatgca gctattgaag atgttttatc aaagccacaa     840
ttgccacttc ccataggact caaacctcca tcaattgaca gtgtgttgaa tgaattacaa     900
cgtcaaggga ttaccaaaat accccccaact tga                                 933

<210> SEQ ID NO 3
<211> LENGTH: 7
<212> TYPE: PRT
<213> ORGANISM: Artificial Sequence
<220> FEATURE:
<223> OTHER INFORMATION: synthetic conserved exon III motif adjacent to
      DNA binding domain of MYB family transcription factors
<220> FEATURE:
<221> NAME/KEY: VARIANT
<222> LOCATION: (4)...(7)
<223> OTHER INFORMATION: Xaa = Ala or Val

<400> SEQUENCE: 3

Ala Arg Glu Xaa Glu Ala Xaa
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic nuclear localization signal (NLS) in
      Solanaceous GLK1

<400> SEQUENCE: 4

Ala Val Glu Gln Leu
1               5

<210> SEQ ID NO 5
<211> LENGTH: 5
<212> TYPE: PRT
<213> ORGANISM: Artificial Sequence
```

```
<220> FEATURE:
<223> OTHER INFORMATION: synthetic modified nuclear localization signal
      (NLS) in Solanaceous GLK2
<220> FEATURE:
<221> NAME/KEY: VARIANT
<222> LOCATION: (3)...(3)
<223> OTHER INFORMATION: Xaa = Glu or Ile

<400> SEQUENCE: 5

Ala Val Xaa Lys Leu
1               5

<210> SEQ ID NO 6
<211> LENGTH: 25
<212> TYPE: DNA
<213> ORGANISM: Artificial Sequence
<220> FEATURE:
<223> OTHER INFORMATION: synthetic PCR amplification primer 1 - SlGLK2
      FL Spec F

<400> SEQUENCE: 6
tatgcttgct ctatcttcat cattg                                          25

<210> SEQ ID NO 7
<211> LENGTH: 20
<212> TYPE: DNA
<213> ORGANISM: Artificial Sequence
<220> FEATURE:
<223> OTHER INFORMATION: synthetic PCR amplification primer 2 - SlGLK2
      exon 2 - R

<400> SEQUENCE: 7
tgagttgcca taagctccaa                                                20

<210> SEQ ID NO 8
<211> LENGTH: 18
<212> TYPE: DNA
<213> ORGANISM: Artificial Sequence
<220> FEATURE:
<223> OTHER INFORMATION: synthetic PCR amplification primer 3 - SlGLK2
      exon 3 - R

<400> SEQUENCE: 8
tttcctccgc ctccgatt                                                  18
```

GLK GENES FOR IMPROVED FRUIT QUALITY

CROSS-REFERENCE TO RELATED APPLICATIONS

This application is a U.S. National Phase of PCT/US2012/059600, filed on Oct. 10, 2012, which claims the benefit of U.S. Provisional Application No. 61/546,934, filed Oct. 13, 2011, the contents of which are incorporated herein by reference in their entirety.

FIELD OF THE INVENTION

The present invention relates to methods for improving fruit quality in plants.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 81906-905474-SE-QLIST.TXT, created on Aug. 11, 2014, 4,567 bytes, machine format IBM-PC, MS-Windows operating system, is hereby incorporated by reference in its entirety for all purposes.

BACKGROUND OF THE INVENTION

Golden2-like (GLK) nuclear transcription factors are known to regulate chloroplast biogenesis in leaf tissues of angiosperms and mosses (Yasumura et al., 2005, *Plant Cell* 17: 1894-1907; Waters and Langdale, 2009, *EMBO J* 28: 2861-2873). While many advances have been made in understanding of leaf chloroplast biogenesis, the role of GLK transcription factors has not been characterized in fruit.

The green tomato fruit pericarp contains photosynthetically active chloroplasts (Piechulla et al., 1985, *Plant Molecular Biology* 5: 373-384; Piechulla et al., 1987, *Plant Physiology* 84: 911-917; Blanke and Lenz, 1989, *Plant Cell and Environment* 12: 31-46; Gillaspy et al., 1993, *Plant Cell* 5: 1439-1451; Carrara et al., 2001, *Photosynthetica* 39: 75-78) and it has been reported that as much as 20% of the total carbon in fruit is a consequence of photosynthetic activity in the green fruit itself. Proteins involved in light harvesting electron transfer and $CO_2$ fixation are present in tomato fruit. While many components of the photosynthetic apparatus are conserved in leaves and fruits, key differences exist, suggesting possible fruit-specific regulation. The photosynthetic mechanisms that are operative in tomato fruit chloroplasts are not clearly defined but anatomical and metabolic differences suggest that fruit-specific mechanisms may be important (Blanke and Lenz, 1989; Hetherington et al., 1998, *Journal of Experimental Botany* 49: 1173-1181; Carrara et al., 2001). For example, many fruit, including tomatoes, lack or have very few stomates, so it is unclear how $CO_2$ is assimilated and regulated in fruit. Tomato fruit can fix $CO_2$ by utilizing ribulose 1,5-bisphosphate carboxylase (RuBPCO) and phosphoenolpyruvate carboxylase (PEPCase), but endogenous respiration in fruit make it difficult to measure net assimilation of $CO_2$ and details of the mechanisms of tomato fruit photosynthesis has not been resolved (Blanke and Lenz, 1989; Hetherington et al., 1998). Chlorophyll, the intact photochemistry of Photosynthesis System 2 (PS2) and the presence of carbon assimilation enzymes suggest that green fruit pericarp chloroplasts contribute to the overall carbon and energy required for fruit development (Smillie et al., 1999, *Journal of Experimental Botany* 50: 707-718). Furthermore, tomato fruit that develop in the absence of light have rudimentary chloroplasts with little or no chlorophyll or thylakoid grana and these fruit exhibit reduced sugars when ripe. This suggests that fruit chloroplasts may contribute to the overall accumulation of sugars by the fruit.

Chloroplast biogenesis is a complex process that requires close co-ordination of plastid and nuclear genomes, and many proteins that accumulate in the chloroplast are encoded by the nuclear genes (Fitter et al., 2002, *Plant Journal* 31: 713-727). Expression of the Golden2-like (GLK) genes, members of the GARP family of MYB transcription factors, is known to be required for chloroplast biogenesis and maintenance in the vegetative tissues of maize, rice and *Arabidopsis* (Fitter et al., 2002; Waters and Langdale, 2009). As has been observed in other plants, *Arabidopsis* has two redundant GLK genes, AtGLK1 and AtGLK2. Mutations in AtGLK1 or AtGLK2 do not alter leaf chloroplast morphology, although the siliques (seed capsules) of the Atglk2 mutant are pale green. Atglk1Atglk2 double mutants have attenuated chloroplast development and all of the leaves of the plants are light green. AtGLK1 regulates photosynthesis in specific cell types (Waters et al., 2008, *Plant Journal* 56: 432-444). In maize, ZmGLK1 and ZmGLK2 (G2) are associated with $C_3$ photosynthesis, but ZmGLK1 is responsible for differentiation in $C_4$ mesophyll cells and ZmGLK2 functions in $C_4$ bundle sheath cells, suggesting cell-type specific regulation of $C_4$ photosynthetic capacity by these transcription factors (Rossini et al., 2001, *Plant Cell* 13: 1231-1244). Partial complementation of the Atglk1 Atglk2 double mutant by the moss *Physcomitrella patens* PpGLK1 gene indicates that GLKs are similar in bryophytes and vascular plants, although because AtGLK1 is unable to complement a Ppglk1 Ppglk2 double mutant, some aspects of the function and/or regulation of GLKs may be species specific.

While the functions of GLK transcription factors have been inferred by examining leaf phenotypes, their role in fleshy green fruit development has not been evaluated. In particular, the art fails to show a link between GLK activity and fruit traits such as starch, soluble solids and/or sugars. The present invention addresses these and other needs.

BRIEF SUMMARY OF THE INVENTION

The present invention provides methods of preparing a cultivated tomato plant having fruit with increased sugar content. The method comprise crossing a first parent cultivated tomato plant with a second parent tomato plant which expresses a functional Golden2-like nuclear transcription factor (GLK) protein in green fruit; and selecting offspring with increased GLK activity in the green fruit compared to the parent cultivated tomato plant. In some embodiments the second parent tomato plant is *Solanum pimpinellifolium* or *Solanum pennellii*. The method of selecting the offspring can be carried out by detecting a GLK gene encoding a full length, functional protein in the green fruit, for example, by PCR. The invention also provides tomato plants made by the methods of the invention.

A plant of the invention may comprise a heterologous nucleic acid sequence encoding a functional GLK that increases chloroplast biogenesis in green fruit of the plant compared to a control plant that lacks the nucleic acid sequence. In some embodiments, the plant is a tomato plant.

The heterologous nucleic acid may be from *Solanum pimpinellifolium* or *Solanum pennellii*.

DEFINITIONS

The term "plant" includes whole plants, shoot vegetative organs and/or structures (e.g., leaves, stems and tubers), roots, flowers and floral organs (e.g., bracts, sepals, petals, stamens, carpels, anthers), ovules, seed (including embryo, endosperm, and seed coat), fruit, seedlings, plant tissue (e.g., vascular tissue, ground tissue, and the like), cells, and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid, and hemizygous.

A polynucleotide sequence is "heterologous" to an organism or a second polynucleotide sequence if it originates from a foreign species, or, if from the same species, is modified from its original form. For example, a polynucleotide sequence that is heterologous to a plant may be introduced into the genome of the plant through a sexual cross or using recombinant techniques.

"Increased" or "enhanced" GLK expression or activity refers to an augmented change in the protein's expression or activity in a plant cell. Examples of such increased activity or expression include, e.g., where GLK expression is increased above control levels and/or where it is ectopically expressed, e.g., in a place or time where it is not expressed in a control plant. In some embodiments, GLK expression or activity is increased above the level of that in wild-type, control plants. In some embodiments, GLK expression or activity can be present in an organ, tissue, or cell where it is not normally detected in wild-type, control plants (e.g., expressed in fruit). Increased GLK expression leads to increased or enhanced chloroplast biogenesis in the plant cell or organ. The levels of chloroplast biogenesis can be measured using techniques known in the art, for example, by measuring total chlorophyll in a tissue as described below.

DETAILED DESCRIPTION

The present invention is based, at least in part, on the discovery that the expression of functional GLK genes affect chloroplast biogenesis in green fruit. As shown here, GLK function can be enhanced in plants with reduced or no GLK activity in green fruit (e.g., in domesticated tomato varieties) and thereby improve ripened fruit traits, such as starch, soluble solids and/or sugar content.

In particular, it has been observed that two conserved GLKs are expressed in the Solanaceae. Solanaceous GLK1s are expressed in leaves but are not detectably expressed in fruit. Solanaceous GLK2s are expressed in fruit as well as in leaves but in domesticated tomato lines, the GLK2 gene encodes a truncated protein.

GLK expression is important for chloroplast development during fruit ontogeny. The results presented here show that expression of GLK genes encoding functional, full length GLK proteins expands the photosynthetic structures within green domesticated fruit chloroplasts and, as a consequence, increases the amounts of the products of photosynthesis and carbon fixation, e.g., starch and eventually soluble sugars, that accumulate in ripe fruit. In *Arabidopsis* and maize leaves, key steps of the chlorophyll biosynthetic pathway are up-regulated by GLK expression and down-regulated by mutations in GLKs (Hall et al., 1998, *Plant Cell* 10: 925-936; Cribb et al., 2001, *Genetics* 159: 787-797; Waters et al., 2008, *Plant J.* 56:432-444; Waters et al., 2009, *Plant Cell* 21: 1109-1128). Chloroplast biogenesis in young domesticated tomato fruit may involve other regulators besides GLKs but green fruit chloroplasts are enhanced by expression of functional GLKs. In pepper fruit, in contrast, CαGLK2 is expressed in fruit and it encodes a full length protein.

Production Of Plants

Plants with increased GLK activity compared to wild type, control plants can be produced by crossing a first plant (e.g., a cultivated tomato) with reduced or no GLK activity in the green fruit with a second plant (e.g., a wild tomato plant) that has higher GLK activity in the green fruit than the first plant. A plant or plant tissue is considered to have no GLK activity if a functional GLK protein, or an mRNA encoding it, cannot be detected using standard techniques. This approach can be used for any plant that can be crossed with a second plant having the desired level of GLK activity in green fruit.

The methods are useful, for example, in increasing GLK activity in green fruit of tomato cultivars. As noted above, many tomato cultivars express non-functional GLK proteins in green fruit. Introgression of a functional GLK gene into a tomato cultivar lacking such a gene can be used to improve fruit quality in the cultivar. Any related species (for example in the genus *Solanum*) which expresses functional GLK in the green fruit can be used to introgress a functional GLK gene into the tomato cultivar. Examples of suitable plants for this purpose include *Solanum pimpinellifolium*, and *Solanum pennellii*, *Solanum habrochaites* (or any variety carrying the U+ allele of the uniform unripe ripening (u) mutation). For example, green shouldered heirloom tomato varieties may be suitable. The following description focuses on methods for improving tomato cultivars. One of skill will recognize that similar approaches can be used for any desired plant.

Tomato accessions with functional full length GLK2s include LA2838A (Ailsa Craig) and LA3030 (Gardener). Accessions with truncated GLK2s include LA0643 (Long Red u), LA3247 (Craigella Ailsa Craig), and LA3035 (Gardener u). All accessions are available from the Tomato Genetics Resource Center at UC Davis.

Chromosome coordinates for GLK2 genes in tomato have been determined. SL2.40 coordinates of the GLK2 coding sequence are ch10:2292050 . . . 2295945 (+strand) according to the current genome sequence of tomato available from Sol Genomics Network (tomato release 2.4).

Standard breeding methods can be used for this purpose. Generally, the methods involve emasculation of one parent, followed by application of pollen from the other parent to the stigma of the first parent. The crosses can be performed using either parent as the pollen parent. Embryo rescue can also be performed if the flowers abort after pollination.

Any of a number of breeding schemes can be used to introgress increased GLK activity into the desired cultivar. The particular scheme used is not critical to the invention, so long as the gene is stably incorporated into the genome of the cultivar.

Any standard method of screening for desired plants can be used, as discussed in more detail below. For instance, plants can be screened by the color of the fruit. Since the plants of the invention have more thylakoid membranes and more chloroplasts, the fruit have a darker green phenotype prior to ripening. The plants may also be screened for the presence of a full length, functional protein encoding GLK gene or gene transcript in the fruit using well known methods, such as polymerase chain reaction (PCR) and polynucleotide sequencing analysis. In addition, increased GLK activity can be detected by measuring chlorophyll content, starch, soluble solids or sugars using the methods described below. Alternatively, marker genes which are tightly linked with the GLK gene can be used to identify the desired plants.

GLK genes can be used to confer the desired phenotype on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna*, and, *Zea*. In some embodiments, the plant is a cultivated tomato *Solanum lycopersicum (Lycopersicon esculentum)*.

Glk Nucleic Acids And Polypeptides

Plant GLK genes have been cloned and described in the literature (e.g., from *Arabidopsis thaliana, Zea mays, Triticum aestivum*, and *Oryza sativa*). Sequences of these genes are provided in GenBank: AtGPR11 GLK1, *Arabidopsis thaliana* GPRI1 (NP_565476.1); AtGLK2, *Arabidopsis thaliana* GLK2 (NP_199232.1); ZmGLK1, *Zea mays* ZmGLK1 (ACG28910.1); ZmG2-like1, *Zea mays* G2-like1 (NP_001105018.1); TaG2-like, *Triticum aestivum* golden 2-like (ABL10089.1); OsG2-like, *Oryza sativa* Japonica Group golden2-like (BAD62070.1); OsGLK2, *Oryza sativa* Japonica Group OsGLK2 (BAD81484.1).

One of skill will recognize that the GLK polypeptides like other proteins, have different domains which perform different functions. Fitter et al. 2002(*Plant J.* 31:713-727) describe the regions in GLKs. GLKs all have a "GCTbox" which is a C terminal domain, primarily in exon VI. This domain is reported to be required for homo and hetero dimerization of the maize GLKs (Rossini et al., 2001 *Plant Cell* 13:1231-1244). They also have a DNA binding domain that is a helix-loop-helix domain that probably forms 3 alpha helices. The DNA binding domain is typical of MYB family transcription factors and is in exon III. Adjacent to the DNA binding domain is the motif AREA/VEAA/V (SEQ ID NO:3) that appears to be well conserved. A nuclear localization signal (NLS) is also present (AVEQL; SEQ ID NO:4) in Solanaceous GLK1s but slightly modified to AVE/IKL (SEQ ID NO:5) in GLK2s; a second nuclear localization signal is reported in *Arabidopsis* GLK2 but that sequence is modified in the Solanaceous GLK2s (Fitter et al., 2002).

Methods For Detecting Functional Glk Genes

The plants of the invention can be tested for expression of functional GLK gene by a number of methods. For example, presence of the introgressed functional GLK gene can be detected using standard molecular biological techniques, such as PCR. In order to identify a functional *Solanum lycopersicon* GLK2 gene (S1GLK2), PCR amplification of a fragment of genomic DNA with the primers 1 -S1GLK2 FL Spec F: TATGCTTGCTCTATCTTCATCATTG (anneals to very beginning of exon 1, to the ATG site) and either of these reverse primers:

2 -S1GLK2 exon 2-R:TGAGTTGCCATAAGCTCCAA (SEQ ID NO:7) (anneals to middle of exon 2).

3 -S1GLK2 exon 3 -R:TTTCCTCCGCCTCCGATT (SEQ ID NO:8) (anneals to middle of exon 3). The resulting fragment can then be sequenced to confirm whether 6 or 7 As are present in the sequence. If there are 6 As then the sequence encodes a full length protein but if there are 7 As then a stop codon in the region results.

In other embodiments, increases in chloroplast biogenesis can be detected by measuring chlorophyll in leaves or mature green fruit using standard techniques, as described below. In addition, the presence of an introduced functional GLK gene can be detected, for example, using PCR and other standard molecular techniques.

Improved fruit quality can be evaluated by measuring starch, soluble solids, and/or sugars using standard techniques as described below. As noted, above the fruit of plants of the invention have increased levels of starch, soluble solids, or sugars, as compared to control plants lacking GLK activity. For example, cultivated tomatoes of the invention bear ripe fruit having soluble solids levels that are at least 10%, usually at least 20% higher, than control plants. The ripe fruit of the plants also have sugar levels (fructose and glucose) at least 10% higher, usually at least 30% higher, than control plants.

EXAMPLES

The following examples are offered to illustrate, but not to limit the claimed invention.

Example 1

To identify GLK genes in three Solanaceaous species, in silico homology searches of tomato and potato EST and genome sequence databases and pepper transcriptome sequence assemblies using *Arabidopsis* AtGLK1 and AtGLK2 revealed two GLK-like genes each in pepper (CαGLK1 and CαGLK2), potato (SpGLK1 and SpGLK2) and tomato (SlGLK1 and SlGLK2). In tomato, SlGLK1 is encoded by Solyc07g053630 on chromosome 7 and SlGLK2 is encoded by Solyc10g008160 located on chromosome 10. The nucleic acid identity between SlGLK1 and AtGLK1 is 43.5% and between SlGLK2 and AtGLK2 is 51%; the amino acid identities for both comparisons are about 46%.

The expression and sequences of the pepper and tomato GLK mRNAs were confirmed by sequencing full length coding region RT-PCR products of RNA prepared from leaves and fruit. GLK1 and GLK2 transcripts were present in cotyledons, sepals and leaves of tomato and leaves of pepper; but only GLK2 transcripts were detected in green tomato fruit and in pepper fruit, suggesting that transcription of GLK2 alone results in the regulation of fruit chloroplast development. However, nucleic acid sequence analysis of the SlGLK2 transcripts in leaves and fruit from domesticated cultivated tomato varieties as well as the SGN release 2.40 *S. lycopersicon* (var. Heinz 1706) tomato genome sequence indicated that SlGLK2 in these varieties encodes a protein that is truncated after about 80 amino acids due to a sequence frameshift 217 by after the ATG start codon; the sequence is out of frame and results in stop codons near the end of exon 1. If an A at nucleotide position ~217 relative to the translational start codon is removed in silico from the SlGLK2 coding sequence, a full length protein highly similar to the potato and pepper GLK2s is predicted. Therefore, tomato fruit from the light green fruited domesticated varieties whose sequences we have examined, Moneymaker, Gardner, Micro-Tom, M82 and H1706, contain a GLK2 gene that encodes a truncated, and presumably nonfunctional, SlGLK2 transcription factor. SlGLK1 encodes a full-length protein in these tomato accessions but it is expressed only in vegetative tissues (e.g., leaves) but not in fruit. We analyzed the SlGLK2 sequences of the wild species *S. pimpinellifolia, S. habrochaites* and *S. pennellii* and they encode full-length proteins and are expressed in fruit. Therefore, we have concluded that domesticated green tomato fruit lacks GLKs, but green fruit from wild species express full length protein encoding, and likely functional, GLK2s. In contrast to tomato, other Solanaceous plants that we have analyzed (pepper and potato) encode apparently functional full length GLK2 proteins and in pepper, CαGLK2 is the only GLK expressed in developing fruit.

Example 2

Sequencing of Solanaceous GLK2 genes encoding non-functional and functional GLKs has revealed a mutation that results in a stop codon and a truncated gene product. As shown in SEQ ID NO: 1, a non-functional GLK2 gene from Craigella contains a sequence of 7 As starting at position 211, as marked there.

Sequence of a functional GLK2 (from *S. pimpinellifolium*, SEQ ID NO: 2) shows a sequence of 6 A's beginning at position 211. This sequence does not include a stop codon and encodes a functional protein. Also highlighted in SEQ ID NO: 2 is a one base change from the Craigella sequence.

Example 3

Using standard breeding techniques, segments of chromosome 10 from *S. pimpinellifolium* and from *S. pennellii* that contain the GLK2 gene have been introduced into domesticated tomato lines (M82, moneymaker) that do not encode functional GLK2. The fruit from these lines have dark green shoulders.

In addition, the relevant part of the GLK2 genes from U+ and u mutant lines have been sequenced. In the three examples of each, the U+ form encodes a functional GLK2 (and the fruit have dark green shoulders) and the u mutant lines have the nonfunctional GLK2 (and the fruit do not have dark green shoulders and are uniformly light green).

It is understood that the examples and embodiments described herein are for illustrative purposes only and that various modifications or changes in light thereof will be suggested to persons skilled in the art and are to be included within the spirit and purview of this application and scope of the appended claims. All publications, patents, GenBank Accessions, and patent applications cited herein are hereby incorporated by reference in their entirety for all purposes.

What is claimed is:

1. A method of preparing a cultivated tomato plant having fruit with increased sugar content, the method comprising:
crossing a first parent *Solanum lycopersicum* tomato plant with reduced or no Golden2-like nuclear transcription factor (GLK2) activity with a second parent tomato plant which expresses a functional GLK2 protein in green fruit, wherein the second parent tomato plant is *Solanum pimpinellifolium, Solanum pennelii*, or *Solanum lycopersicum* carrying a U+ allele of the uniform ripening locus; and
selecting offspring with increased GLK2 activity in the green fruit compared to the first parent tomato plant.

2. The method of claim 1, wherein the second parent tomato plant is *Solanum pimpinellifolium*.

3. The method of claim 1, wherein the second parent tomato plant is *Solanum pennellii*.

4. The method of any one of claims 1 to 3, wherein the step of selecting the offspring is carried out by detecting a GLK gene encoding the functional GLK protein in the green fruit.

5. A cultivated tomato plant comprising a heterologous Solanaceous GLK2 gene encoding a functional GLK that increases chloroplast biogenesis in green fruit of the plant compared to a control plant that lacks the nucleic acid sequence, wherein the heterologous Solanaceous GLK2 gene is from *Solanum pimpinellifolium* or *Solanum pennellii*.

6. The method of claim 1, wherein the second parent tomato plant is *Solanum lycopersicum* carrying the U+ allele of the uniform ripening locus.

* * * * *